United States Patent
Longton

(10) Patent No.: US 7,076,820 B2
(45) Date of Patent: Jul. 18, 2006

(54) DIAGNOSTIC IMAGING TABLETOP

(75) Inventor: Wallace A. Longton, Mechanicsburg, PA (US)

(73) Assignee: DIACOR, Inc., Salt Lake City, UT (US)

(*) Notice: Subject to any disclaimer, the term of this patent is extended or adjusted under 35 U.S.C. 154(b) by 50 days.

(21) Appl. No.: 10/892,733

(22) Filed: Jul. 16, 2004

(65) Prior Publication Data

US 2004/0255383 A1    Dec. 23, 2004

Related U.S. Application Data

(63) Continuation-in-part of application No. 10/191,185, filed on Jul. 8, 2002, now Pat. No. 6,907,629.

(60) Provisional application No. 60/305,591, filed on Jul. 13, 2001, provisional application No. 60/325,323, filed on Sep. 27, 2001.

(51) Int. Cl.
*A61N 5/00* (2006.01)

(52) U.S. Cl. .......................... 5/601; 378/209
(58) Field of Classification Search ............ 5/601, 5/612, 187, 724; 378/177, 209
See application file for complete search history.

(56) References Cited

U.S. PATENT DOCUMENTS

| | | | |
|---|---|---|---|
| 3,111,582 A | 11/1963 | Levi | |
| 3,428,307 A * | 2/1969 | Alfred | 5/601 |
| 3,466,439 A | 9/1969 | Setala | |
| 3,751,028 A * | 8/1973 | Scheininger et al. | 5/601 |
| 4,991,243 A * | 2/1991 | Rottermann | 5/600 |
| 5,207,688 A | 5/1993 | Carol | |
| 5,226,070 A | 7/1993 | Ariba et al. | |
| 5,537,452 A | 7/1996 | Shepherd et al. | |
| 5,537,454 A * | 7/1996 | Korver, II | 378/65 |
| 5,577,503 A * | 11/1996 | Bonutti | 600/415 |
| 5,622,187 A | 4/1997 | Carol | |
| 5,632,275 A | 5/1997 | Browne et al. | |
| 5,754,997 A | 5/1998 | Lussi et al. | |
| 5,778,047 A * | 7/1998 | Mansfield et al. | 378/209 |
| 6,143,003 A | 11/2000 | Cosman | |
| 6,161,237 A | 12/2000 | Tang et al. | |
| 6,493,417 B1 | 12/2002 | Baer et al. | |
| 6,907,629 B1 * | 6/2005 | Longton et al. | 5/601 |

FOREIGN PATENT DOCUMENTS

| | | |
|---|---|---|
| DE | 38 28 087 A1 | 2/1990 |
| WO | WO 88/03004 | 5/1988 |
| WO | WO 88/03779 | 6/1988 |

OTHER PUBLICATIONS

Supplementary European Search Report, dated Apr. 29, 2005.

* cited by examiner

*Primary Examiner*—Michael Trettel
(74) *Attorney, Agent, or Firm*—TraskBritt, PC

(57) ABSTRACT

In accordance with the present invention, a tabletop is provided for positioning a patient for diagnostic imaging of a body part. The tabletop preferably rests on a diagnostic imaging table for supporting a patient during diagnostic imaging. The tabletop is defined by (a) a top support surface for supporting a patient being imaged and (b) a bottom support surface for contacting the diagnostic imaging table. A recess, defined in the top support surface, is configured to accommodate a patient support. The recess has a depth sufficient for allowing for vertically positioning a patient on the patient support.

21 Claims, 7 Drawing Sheets

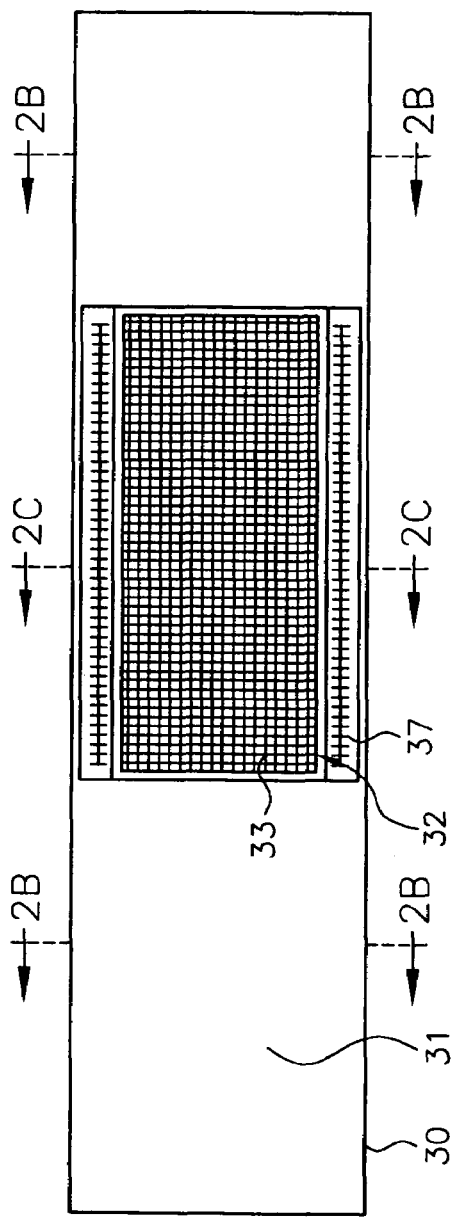
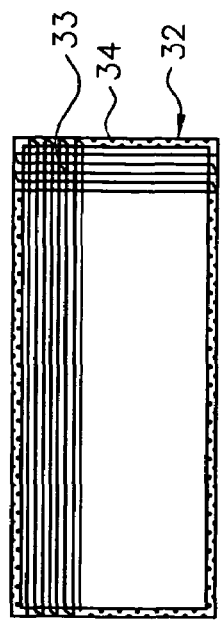
FIG. 2A
FIG. 2B
FIG. 2C
FIG. 2D

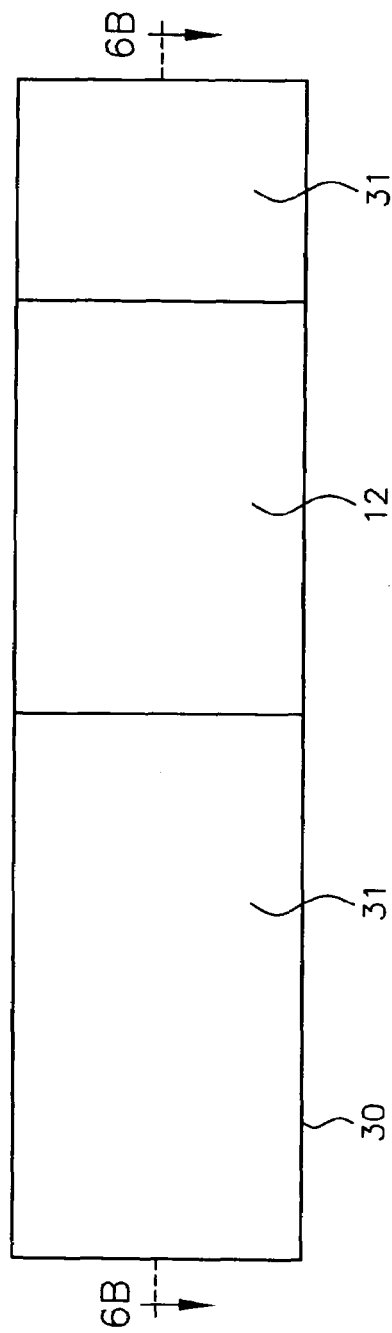
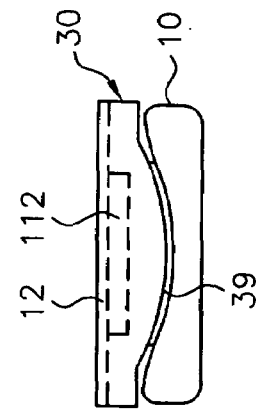
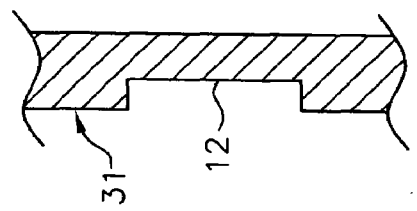
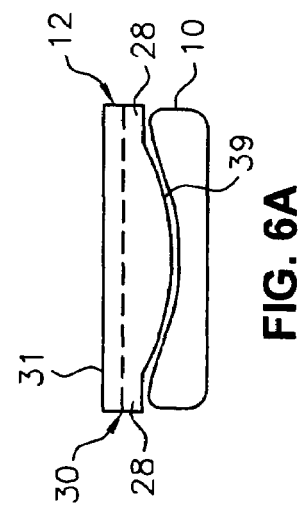
FIG. 6
FIG. 6A
FIG. 6B
FIG. 6C

DIAGNOSTIC IMAGING TABLETOP

The present application is a continuation-in-part of U.S. Ser. No. 10/191,185 filed Jul. 8, 2002, now U.S. Pat. No. 6,907,629, which claims benefit of provisional application U.S. Ser. No. 60/305,59 filed Jul. 13, 2001 and provisional application U.S. Ser. No. 60/325,323 filed Sep. 27, 2001.

BACKGROUND OF THE INVENTION

This invention relates to diagnostic imaging, and particularly, computed topography (CT) scanning. In particular, the invention relates to a tabletop useful for accurate positioning of a patient for diagnostic imaging, so that patient positioning in subsequent medical treatments, such as radiation therapy, accurately and precisely correlates with the imaging data.

Patient positioning systems are used for accurate and reproducible positioning of a patient for radiation therapy, surgery, and other medical procedures. During these procedures, it is common to immobilize a part or parts of the patient's body. Accurate positioning of the body part is also important in initial and subsequent treatments, so that precisely the same location of the body is exposed to the radiation each time. Therefore, different types of devices have been made to immobilize body parts and to index the body to the treatment table to assure proper and repeatable alignment for radiation therapy.

As radiation therapy becomes more precise with procedures such as 3D conformal and Intensity Modulated Radiation Therapy (IMRT), it is critical that all facets of treatment planning are handled with maximum accuracy. Presently, when advanced, highly technical radiation therapy is performed, an imaging scan, such as computed topography (CT), is obtained with the patient "in treatment position." From this scan, not only are the fields and blocking designed, but the treatment plan is calculated.

The standard CT scan table has a hard, concave upper patient support surface, as generally indicated in FIG. 1C below. In practice, this table is provided with a flexible mat which conforms to the upper concave surface of the table, the primary purpose of which is to improve patient comfort during extended scanning. While this configuration contributes to patient comfort, the concave cross-sectional support surface of the table makes it difficult or impossible to exactly index the scanning data obtained with the conditions that will subsequently be encountered during radiation treatment.

CT scans have also been performed on a standard CT scan "flat tabletop insert" to enable better positioning of the patient for advanced treatments. The flat tabletop inserts raise the patient above the level of the sidewalls of the CT table as shown in FIG. 1C, facilitating scanning of the entire body. This table insert is flat, very hard, allows for negligible deflection (defined as the downward movement of the tabletop) under weight of the patient, and tends to flatten the body parts to be imaged. However, in subsequent radiation oncology procedures, a mesh section of the typical radiation oncology table is usually in place in the simulator/linear accelerator during treatment setup and treatments. When positioning a patient for treatment, a deflection of the mesh occurs under weight of the patient, which can be 0.3 cm to as much as 2 to 3 cm at the maximum point.

Lack of accurate position representation at the time of the CT scan will not allow advanced radiation therapy to be as accurate as possible. Higher accuracy can be obtained if the scan is performed directly in accordance with the shape and position of the patient when positioned on the linear accelerator table, especially as the accuracy in IMRT and the like equipment improves and provides greater accuracy and adjustability in treatment and treatment planning.

Current problems with accurate and precise patient positioning for radiation therapy include deflection in treatment/simulator table that is different from deflection in a table used for imaging, variations in patient location on the linear accelerator table varying from day to day, lack of alignment (leveling) of table inserts used in imaging, and the fact that many facilities have already purchased and scan using table inserts that do not possess deflection capabilities. The difference in vertical deflection between the flat CT scan table insert and the use of a flexible treatment mesh to support the body part to be imaged, such as a tumor, may cause a change in the appearance and/or spatial position of the tumor or body part. Every CT, simulator, and linear accelerator deflection should match if the patient is to be treated accurately and reproducibly.

SUMMARY OF THE INVENTION

In accordance with the present invention, a tabletop is provided for positioning a patient for diagnostic imaging of a body part. The tabletop preferably rests on a diagnostic imaging table for supporting a patient during diagnostic imaging. The tabletop is defined by (a) a top support surface for supporting a patient being imaged, (b) a bottom support surface for contacting and supporting the tabletop on a diagnostic imaging table, and (c) a recess, defined in the top support surface of the tabletop, which is configured to accommodate a patient support, specifically a support for the body part to be imaged. The recess has a depth sufficient to allow for vertical positioning and alignment of a patient on the patient support relative to the position of the top support surface of the tabletop.

According to another aspect of the present invention, a flexible patient support panel may be coupled to the tabletop and positioned at least partially within or over the recess. The panel is configured for a vertical deflection in response to positioning a patient on the panel. The recess has a depth sufficient to allow vertical alignment of the flexible support panel in a constant fixed relationship with respect to the top surface of the tabletop.

Additionally, yet another embodiment provides a method for supporting a patient on a diagnostic imaging table for and during diagnostic imaging where the tabletop rests on a diagnostic imaging table. A patient support is retained at least partially within, or over, a recess formed in a top support surface of the tabletop, allowing vertical alignment of the patient on the patient support relative to the position of the top support surface of the tabletop. The patient can be positioned on the tabletop whereby his body extends at least partially over the recess and is held in a fixed position for imaging by the patient support. A method of manufacturing the tabletop is also provided.

While the present invention is primarily described with reference to CT scans, it is equally applicable to other imaging technologies and methods, for example, magnetic resonance imaging (MRI), nuclear medicine (molecular imaging), positron emission topography (PET), and ultrasound.

BRIEF DESCRIPTION OF THE DRAWINGS

FIG. 2 is an illustration of a tabletop of the invention in which the tabletop contains a flexible, indexed patient support panel or section.

FIG. 6 is an overhead view of the tabletop having a recess extending across the entire width of the tabletop.

FIG. 6A is an end view of the tabletop of FIGS. 5 and 6, having a recess extending across the entire width of the tabletop and showing the tabletop installed and resting on a typical CT scan table.

FIG. 6B is a longitudinal cross sectional view along the centerline of the tabletop of FIG. 6A and having a recess extending across the entire width of the tabletop.

FIG. 6C is an end view of the tabletop of FIG. 6, having a first recess extending across the entire width of the tabletop, in which the area of the recess is provided with an optional secondary recess defined by the upper surface and within the area of the first recess.

DETAILED DESCRIPTION OF THE INVENTION

Figure 1A:
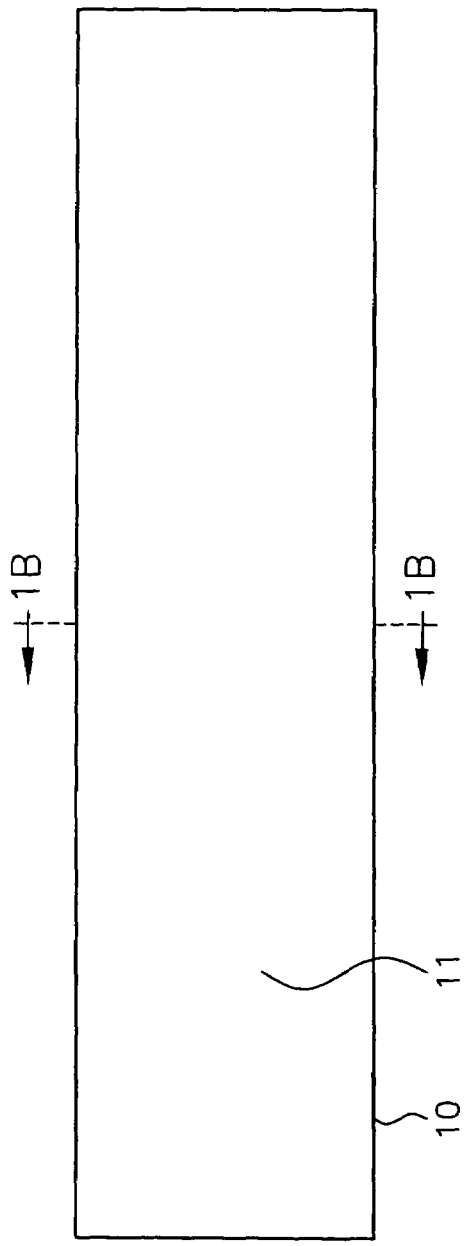
FIG. 1 is an illustration of a typical prior art CT scan table and table insert.
Figure 1B:

In the description which follows the present invention is described with particular reference to the typical CT scan table illustrated generally in FIGS. 1A and 1B. The table 10 has a concave top surface 11 upon which a patient rests. A soft cushion and/or a sanitary covering (not shown) can be placed on the concave top surface 11 of the table. The concavity of the upper surface 11 prevents effective imaging of body parts resting on concave surface 11 in that it complicates correlation of imaging data to conditions which will be encountered during treatment.

Figure 1C:
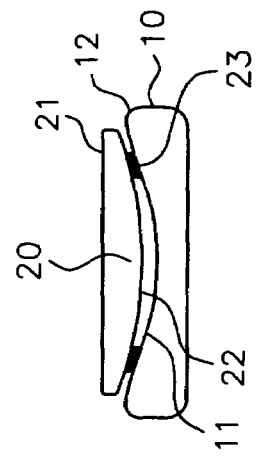

FIG. 1C illustrates a typical CT scan table 10, upon which a flat-top insert 20 has been placed, for the purpose of raising the position of a patient for more accurate imaging. As shown in FIG. 1C, the tabletop insert has a hard, inflexible flat upper patient support surface 21 and a convex lower surface 22 substantially conforming to the concavity of the CT scan table 10. It is positioned on and above the concave surface on support pads 23 which are mounted on lower surface 22. As shown in the drawing, upper surface 21 is elevated above and overlaps sidewalls 12 of the CT tabletop.

Figure 3:
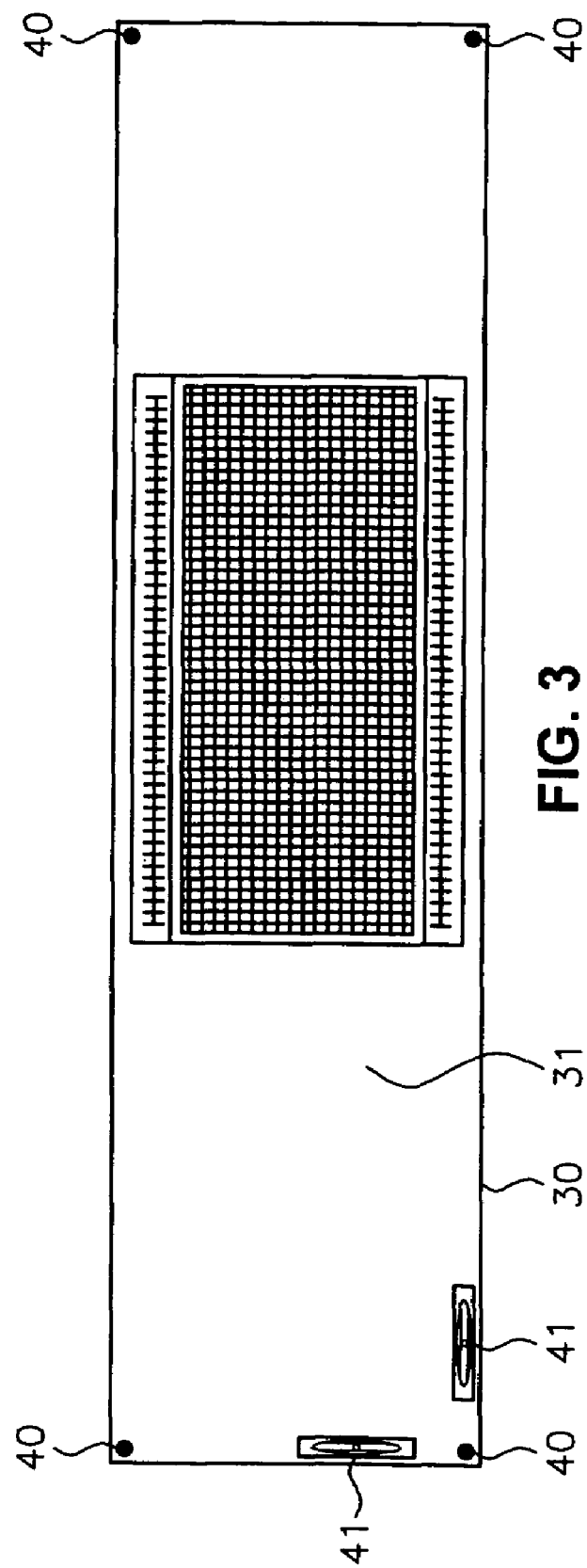
FIG. 3 is an illustration of a tabletop insert of the invention in which the tabletop contains a flexible, indexed patient support panel or section and means for leveling the tabletop in a horizontal position.
Figure 4:
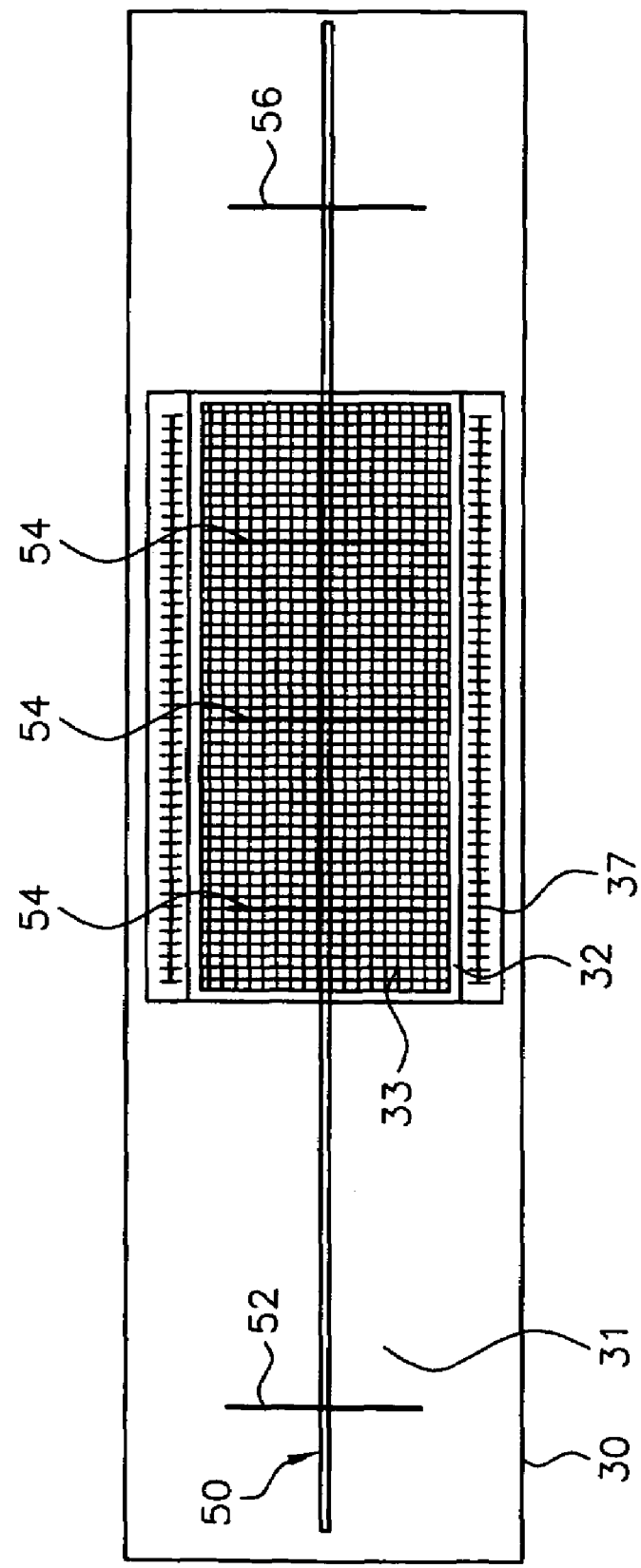
FIG. 4 is an illustration of a tabletop of the invention in which patient position markers are shown.

A tabletop of the present invention, which is particularly useful for accurate and precise repeated patient positioning for diagnostic procedures, is illustrated in FIGS. 2, 3 and 4. FIG. 2A illustrates a tabletop 30 having a flat (planar) upper patient support surface 31, a width less than the width of an aperture in an imaging device through which the tabletop must travel for imaging of body parts and a length sufficient to support a patient thereon. Tabletop 30 of the present invention also has a defined bottom surface which is suitably but not necessarily parallel to the top surface 31.

A section of tabletop 30 has a flexible support panel 32 for the body part to be imaged. The flexible support component 33 of the panel is necessarily made of a radiolucent flexible component, which can be material, fabric, or mesh. Suitable radiolucent materials include, but are not limited to carbon fiber, plastic, rubber, nylon, fiberglass, or other materials well-known in the art.

The flexible support component 33 is tensioned to provide a predetermined vertical deflection when a patient is positioned thereon. The vertical deflection is predetermined to match the vertical deflection of a flexible patient support portion of a treatment simulator or linear accelerator and is generally in the range of up to 0.5 to 2 cm at the maximum point of deflection when the weight of a patient is positioned thereon. To further insure accuracy in deflection of flexible support 33, a stop may be positioned below the bottom surface of the tabletop to limit deflection of flexible support 33.

The flexible support panel 32 of the invention may be permanently mounted in the tabletop or is a removable piece, which can be removed from the tabletop 30 and replaced with a solid insert, or with another flexible support panel of compatible size and shape, if so desired.

The removable flexible support panel may, for example, be sized such that it may be placed on an appropriately configured irradiation treatment table for radiation treatments. Thus, the removable support panel may be configured so that the same support, or similarly configured supports can be used for both imaging and radiation treatment procedures. The ability for interchanging the flexible support panel between the imaging and treatment tables provides additional consistency in the patient positioning for precise treatment application.

Typically, however, the flexible support panel consists of a flexible component 33, as described above and shown in FIG. 2C, connected to a frame 34, as illustrated in FIG. 2D. The flexible component 33 can be tensioned on the frame 34 to adjust the amount of deflection upon load bearing. For example, a suitable string or yarn may be strung through holes in the frame 34 of panel 32 similar to the stringing of a tennis racket, as shown in FIG. 2D. In another embodiment, a fabric used as the flexible component 32 may be held in place on the frame 34 with a groove and spline, similar to the way a screen window is fixed to a frame. Other methods for affixing the mesh to the frame will be apparent to those skilled in the art. A tabletop 30 of the invention may also be designed such that the flexible support panel 33 is an integral, non-removable part of tabletop 30. In such an embodiment, flexible support 33 is directly attached to tabletop 30. In this embodiment, flexible support 33 may be tensioned to provide a predetermined deflection and may be made of materials as described above.

Tabletop 30 of the invention may be designed to accept support panel 32, in much the same way a screen window fits into a window opening in a house. There may be an opening in tabletop 30, wherein the periphery of the opening has rabbet edges to accept a mating surface of support panel frame 34. Alternatively, the opening in the tabletop 30 may be beveled, with the wider portion of the bevel at the top surface 31, and a corresponding bevel on the outer edges of frame 34 to mate with the corresponding bevel in the tabletop. Other well known means for retaining the frame in the tabletop opening will be apparent to those skilled in art. Regardless of the means used for retaining the frame in the tabletop. In a typical embodiment of the invention, the flexible support panel 32 will remain approximately flush with the plane of the top surface 31 of the tabletop. However, the flexible support panel 32 may rest lower or higher than the plane of the top surface 31 of a tabletop of the present invention.

Tabletop 30 of the present invention also has, along the perimeter of the flexible support panel 32, a means for indexing 37 the exact position of a patient relative to the length and optionally the width of the support panel. An indexing means or ruler 37 may be provided along at least one edge of support panel 32, and may extend around the perimeter of the support panel. In one embodiment, an indexing means 37 may be part of or attached to the upper surface 31 of tabletop 30. In another embodiment, indexing means 37 may be part of or attached to the frame of flexible support panel 32. In any embodiment, indexing means 37 may be either radiolucent or radiopaque.

The support panel 32 is preferably adapted to be positioned in the tabletop 30 so that the center of the support panel is in alignment with the longitudinal center of the tabletop. In another aspect of the invention, the longitudinal center of the tabletop is provided with a visible radioopaque support marking extending along the center of the tabletop and along the centerline of the support panel, as shown at 50 of FIG. 4. There may be one or more such longitudinal lines, but one of them must extend down the centerline of the table and the support panel. One or more lateral support markings extend laterally across the flexible support to perpendicularly cross and intersect the longitudinal centerline support marking 50, as shown generally at 54 of FIG. 4, one of which is positioned at the center line of longitudinal axis of the support panel. The longitudinal and lateral support marks are preferably a visible coating on the surface of the flexible support, and are radiopaque. Radiopaque markers are preferred if it is desired to relate the patient's position relative to the support in the radioimages.

Radiopaque markers would be helpful to practitioners when, for example, the patient is aligned with the visible markers 54 on the flexible support panel, and the patient alignment is recorded or noted. A patient's position may be recorded by simply applying a mark on the patient's body at the location where the patient's skin contacts the positioning markers 54 on the support panel. However, when the positioning markers are radiopaque, any adjustment in the patient's position on the tabletop may be accurately assessed relative to the location of the markers on the radioimage. In each case, the peripheral markings and/or the centerline and/or lateral support markings may contain lettered or numerical designations indicating relative lateral or longitudinal position of the patient on the support panel.

A tabletop of the present invention may also have a lateral guide rail composed of a fixed portion 35 extending downward from the outside edge of the bottom of the tabletop and a stiff, yet flexible slide rail 36 extending inward from the fixed portion 35, below the bottom of the tabletop, as illustrated in FIG. 2B. Both the lateral guide rail and the slide rail may extend along the entire length of the tabletop. The fixed portions 35 of the lateral guide rail may be designed to rest over and in close proximity to the outer edge of an existing table of a diagnostic scanning instrument upon which the tabletop of this invention is to be placed. The flexible inner portions 36 of the slide rail may be designed to rest on the outer top edge of an existing table of a diagnostic scanning instrument to facilitate lengthwise movement and adjustment along the length of the table.

It will be appreciated that the embodiment of the invention, such as that illustrated in FIG. 2 may be an overlay, i.e., a table insert (tabletop) for an existing imaging table. Likewise it may itself be a table top which is supported by a base suitable for supporting and leveling the table top and having other suitable mechanisms appropriate for imaging procedures, including operative components which interact with the table top to transport it into and out of the imaging device.

FIG. 3 illustrates another embodiment of the present invention. In this embodiment, a tabletop 30 may have leveling means 40 and 41 for adjusting the horizontal plane of the entire tabletop. Leg-type leveling means 40 may be embedded in the corners of the tabletop and extend downward from the bottom of the tabletop. Leveling legs 40 may extend downward from the bottom, either perpendicular to the tabletop or at an angle less than 90° but greater than 0°. Leveling legs 40 should be designed to provide sufficient clearance for deflection of the flexible insert portion 33. In addition, the leveling means also includes at least one longitudinal level indicator and one lateral level indicator positioned on or in the surface of the tabletop. This embodiment is particularly suited for use as a tabletop to overlay an existing imaging table, facilitating appropriate leveling of the patient support surface independent of the leveling of the imaging table.

Figure 5:
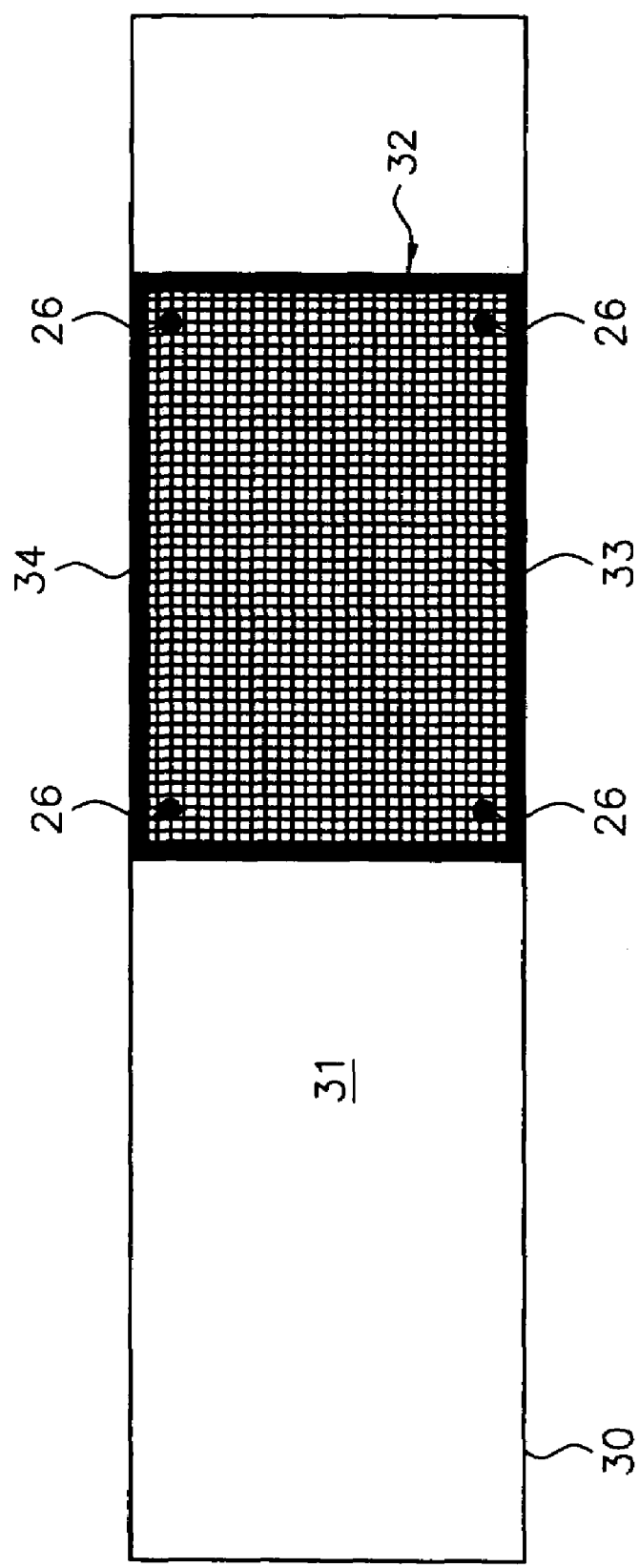
FIG. 5 is an overhead illustration of the table assembly depicting a tabletop with flexible patient support panel in place within a recess in the top surface of the tabletop.

According to an additional embodiment of the invention, FIG. 5 illustrates an imaging tabletop assembly. The assembly comprises tabletop 30 and a patient support 33, such as that shown in FIG. 2D and described above in detail, mounted in or over a recess (not shown in FIG. 5) in top support surface 31. As shown, the patient support comprises a flexible patient support panel 32 which extends laterally across substantially the entire width of tabletop 30, with flexible component 33 affixed to frame 34.

The flexible support panel may be secured to tabletop 30 with at least one pin 26 for frame retention of the support panel on the tabletop. Such pins may be provided at any position or orientation suitable for retention of the support panel on the tabletop. Pin 26 can be substituted with any type of material used for securing connections between one or more types of structures. Suitable materials include, but are not limited to staples, nails, hooks, or other materials well-known in the art. Alternatively, as discussed further below, the recess 12 may be surrounded on all sides by the top surface of the tabletop, in which case the walls of the recess 12 themselves act to retain the flexible support panel in place on the tabletop. The patient support may also comprise a support structure for other body parts to be imaged, for example a head support, a neck support, a chest support, such support structures being adapted for mounting in the recess and for vertical alignment and positioning relative to the top surface of the tabletop.

In an exemplary embodiment, the width of tabletop 30 may be such that its lateral edges are flush and align with the lateral edges of the imaging table when the tabletop is in place and properly aligned on the imaging table, but may be wider or narrower depending on the width of the imaging table and the opening through which the tabletop must pass for imaging of a body part. The length of the tabletop 30 must be sufficient to support a patient thereon, but in general is suitably no longer than the tabletop on which it is designed to rest. Depending on its length and adaptations for mounting on the imaging table, the tabletop may be adjustable longitudinally along the length of the imaging table 10 on which it rests so that the recess 12 and any patient supports mounted therein are within imaging range when the table 10 travels into the imaging device. Additionally, the tabletop may be adapted for locking engagement with the imaging table so that the tabletop is in a fixed position relative to the imaging table. The locking means may be positioned on the tabletop, the imaging table to which the tabletop is affixed, or interlocking means on both the tabletop and the table. Any suitable locking mechanism (not shown) may be utilized, and such locking mechanisms are within and apparent to those skilled in the art.

As illustrated in FIG. 6, tabletop 30 comprises a recess 12 surrounded and defined on at least two sides by top support surface 31, suitably wherein recess 12 extends across the entire width of tabletop 30. Recess 12 defines the area of tabletop 30 arranged to receive a patient support such as patient support panel 33 (shown in FIG. 5). Recess 12 may be any size suitable for receiving and retaining the patient support and may be round, oval, square, or rectangular. The depth of recess 12 is sufficient to facilitate vertical alignment of the patient support relative to the top support surface 31 of the tabletop. Typically that depth may be in the range of from about 0.75 to about 2.0 inches, the depth suitably being substantially the same as the depth of a patient support panel. Additionally, as shown in FIG. 6C, tabletop 30 may be provided with an secondary recess 112 for receiving or mounting other patient support structures, such as a head restraint, in particular those accessories which require additional depth in order to achieve proper vertical alignment of the body part to be imaged relative to the top support surface 31 of tabletop 30.

FIG. 6A further illustrates an exemplary embodiment of a cross-sectional view of tabletop 30 in which recess 12 extends across the entire width of tabletop 30. In FIG. 6A the tabletop 30 is shown resting on a conventional CT scan table 10. In this embodiment tabletop 30 has a flat (planar) top support surface 31 which defines the recess 12 on two sides, namely at the proximal and distal ends of recess 12 as shown in FIG. 6B. Below the sides of recess 12 and top support surface 31 shoulders 28 define the lateral edges and width of tabletop 30 then extend inwardly from the edge of tabletop 30 to form a convex bottom surface 39. Convex bottom surface 39 is suitably arched to mate snugly with and rest upon the concave upper surface of imaging table 10. Bottom surface 39 can be continuous along the length of imaging table 10 upon which it is designed to rest. Moreover, the width of the tabletop 30 as shown is such that the lateral edges of shoulders 28 are approximately flush with the corresponding lateral edges of the imaging table 10 on which tabletop 30 rests for imaging a patient.

As a practical matter recess 12 may be of any depth suitable for mounting and retention of a patient support, and the total depth of the tabletop will be relatively greater than the depth of recess 12. However, it will be appreciated by one skilled in the art that the recess must be sufficiently shallow to preserve the rigidity and strength of the tabletop 30 and prevent significant flexing of the tabletop 30 when a patient is positioned thereon. As noted above, if additional depth is required for a particular application, that additional depth may be provided by providing a secondary recess 112 as shown in FIG. 6C.

Figure 7:
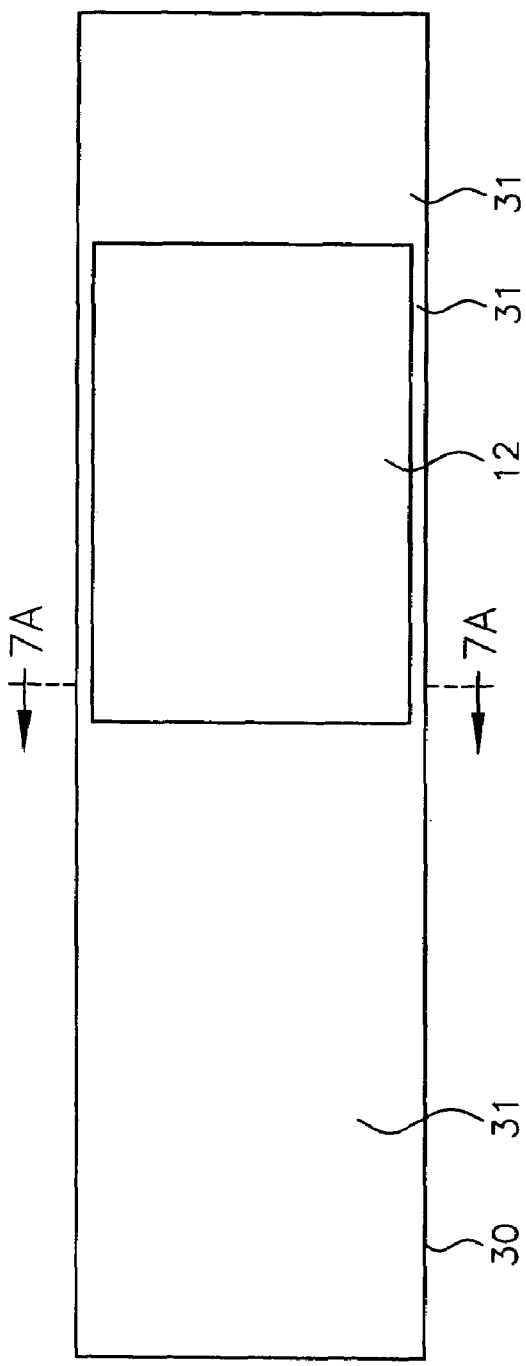
FIG. 7 is an overhead view of the tabletop having a recess extending between and defined on all sides by the top support surface of the tabletop.
Figure 7A:
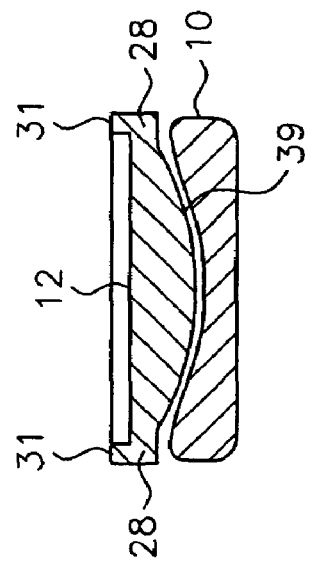
FIG. 7A is a cross sectional view of the tabletop of FIG. 7, having a recess extending between and defined on all sides by the top support surface of the tabletop.

In yet another exemplary embodiment, as illustrated in FIG. 7, tabletop 30 may be designed having a flat (planar) upper patient support surface 31, a width less than the width of an aperture in an imaging device through which tabletop 30 must travel for imaging of body parts, and a length sufficient to support a patient thereon. Tabletop 30 is provided with bottom surface 39 (FIG. 7A) which comprises a convex arch the curvature of which adapted to mate with the upper concave surface of the imaging table 10 on which the tabletop rests for and during imaging. Tabletop 30 is provided with recess 12, as shown in FIG. 7A. Recess 12 is as shown in FIG. 7, defined and at least at least partially surrounded along all sides by the walls of recess 12 which extend downwardly from top surface 31. However, it will be appreciated by one skilled the art that the purposes of having the lateral edges of recess 12 is to provide built in lateral walls for retention of a patient support in recess 12. Accordingly, in a variation (not shown) which will be apparent to those skilled in the art, the lateral walls of recess 12 may be only partially defined by walls extending downwardly from top surface 31, with the remaining lateral portions of recess 12 extending the full width of tabletop 30.

Except as specifically indicated above, the general principles set forth above with respect to the embodiments shown in FIGS. 1-4 are equally applicable to the embodiments of FIGS. 5-7.

While the present invention is primarily described with reference to CT scan tables, it is equally applicable to other imaging technologies and methods, for example, magnetic resonance imaging (MRI), nuclear medicine (molecular imaging), positron emission topography (PET), and ultrasound.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. An apparatus configured for use with a diagnostic imaging table to support a patient during diagnostic imaging, said apparatus comprising:
   a tabletop configured to rest on a diagnostic imaging table, said tabletop having a bottom support surface comprising a convex portion along the longitudinal axis of the tabletop and configured for contact with the diagnostic imaging table and a top support surface configured to support a patient being imaged; and
   a recess defined in said top support surface of said tabletop and configured to accommodate a patient support, said recess having a depth sufficient to allow vertical alignment of said patient support relative to said top support surface.

2. The apparatus of claim 1 wherein said bottom support surface of said tabletop defines at least one shoulder extending laterally from said convex portion.

3. The apparatus of claim 1 wherein said recess extends fully across a width of said tabletop.

4. The apparatus of claim 3 wherein said tabletop comprises a plurality of pins extending from said tabletop and adapted for retaining said patient support in a defined position in the recess of said tabletop.

5. The apparatus of claim 1 where said recess is defined on all sides by vertical walls extending downward from said top support surface.

6. The apparatus of claim 1 further comprising a recess for a flexible patient support panel and a secondary recess for other patient supports.

7. An apparatus configured for use with a diagnostic imaging table to support a patient during diagnostic imaging, said apparatus comprising:
   a tabletop configured to rest on a diagnostic imaging table, said tabletop having a bottom support surface configured for contact with the diagnostic imaging table and a top support surface configured to support a patient being imaged;
   a recess defined in said top support surface of said tabletop; and a flexible support panel coupled to said tabletop and positioned at least partially within or over said recess, said flexible support panel being configured for a vertical deflection in response to positioning a patient on said flexible support panel, said recess having a depth sufficient to allow vertical alignment of said patient support relative to said top support and a plurality of pins extending from said tabletop and adapted for retaining the flexible support panel in a fixed position in the recess.

8. The apparatus of claim 7 wherein said bottom support surface of said tabletop comprises a convex portion.

9. The apparatus of claim 8 wherein said bottom support surface of said tabletop defines at least one shoulder extending from said convex portion and defining the width of said tabletop.

10. The apparatus of claim 7 wherein said recess extends fully across a width of said tabletop.

11. The apparatus of claim 7 further comprising a recess for said patient support panel and a secondary recess for other patient supports.

12. A method of supporting a patient on a diagnostic imaging table during diagnostic imaging, said method comprising the steps of:

resting a tabletop having a bottom portion comprising a convex portion on a diagnostic imaging table;

retaining a patient support at least partially within or over a recess formed in a top support surface of the tabletop, thereby allowing vertical alignment of said patient support relative to said support surface; and positioning the patient on said tabletop such that said patient extends at least partially over the recess, then imaging the body part positioned over said patient support.

13. The method of claim 12 further comprising the step of positioning the body part to be imaged on said patient support.

14. The method of claim 13 further comprising the step of positioning the body part to be imaged on a flexible patient support panel.

15. The method of claim 13 further comprising the body part to be imaged on a patient support comprising a head restraint.

16. The method of claim 13 further comprising the step of positioning the body part to be imaged on a patient support comprising a chest support.

17. The method of claim 13 further comprising the step of positioning the body party to be imaged on a patient support comprising a neck support.

18. A method of manufacturing an apparatus configured for use with a diagnostic imaging table to support a patient during diagnostic imaging, said method comprising the steps of:

forming a tabletop having a bottom support surface configured for contact with the diagnostic imaging table and a top support surface configured to support a patient being imaged1 wherein the bottom support surface comprises a convex lower support surface having a curvature substantially the same as a convex curvature of the diagnostic imaging table on which the tabletop rests for imaging of a body part; and forming a recess in said top support surface of said tabletop with a depth sufficient to allow vertical alignment of a patient support relative to said top support surface.

19. The method of manufacturing set forth in claim 18, wherein said concave bottom support surface terminates in lateral shoulders which define the width of the imaging tabletop.

20. The method of manufacturing set forth in claim 18, which further comprises forming a recess that extends fully across the width of said tabletop.

21. The method of manufacturing set forth in claim 18, which further comprises forming a recess that is fully surrounded by walls extending downwardly from said top support surface on all sides of such recess.

\* \* \* \* \*